US012685519B2

(12) United States Patent
Nemeth et al.

(10) Patent No.: US 12,685,519 B2
(45) Date of Patent: *Jul. 21, 2026

(54) ORAL FLUID COLLECTION DEVICE

(71) Applicant: ORASURE TECHNOLOGIES, INC., Bethlehem, PA (US)

(72) Inventors: Attila Csaba Nemeth, Ontario (CA); Adele Jackson, Ontario (CA); Koen Catharina Lodewijk Beyers, Wuustwezel (BE)

(73) Assignee: ORASURE TECHNOLOGIES, INC., Bethlehem, PA (US)

( * ) Notice: Subject to any disclaimer, the term of this patent is extended or adjusted under 35 U.S.C. 154(b) by 390 days.

This patent is subject to a terminal disclaimer.

(21) Appl. No.: 18/556,212

(22) PCT Filed: Mar. 31, 2022

(86) PCT No.: PCT/US2022/022741
§ 371 (c)(1),
(2) Date: Oct. 19, 2023

(87) PCT Pub. No.: WO2022/231756
PCT Pub. Date: Nov. 3, 2022

(65) Prior Publication Data
US 2024/0180531 A1     Jun. 6, 2024

Related U.S. Application Data

(60) Provisional application No. 63/179,780, filed on Apr. 26, 2021.

(51) Int. Cl.
*A61B 10/00*          (2006.01)

(52) U.S. Cl.
CPC .... *A61B 10/0051* (2013.01); *A61B 2010/009* (2013.01)

(58) Field of Classification Search
CPC .............. A61B 10/0051; A61B 10/007; A61B 10/0096; A61B 10/0283; A61B 2010/0006; A61B 2010/0009; A61B 2010/0074; A61B 2010/0258; A61B 2562/0295;
(Continued)

(56) References Cited

U.S. PATENT DOCUMENTS

| | | | |
|---|---|---|---|
| 8,025,851 | B2 | 9/2011 | Slowey |
| 8,992,482 | B2 | 3/2015 | Fojtik |
| 9,198,641 | B2 | 12/2015 | Slowey |

(Continued)

FOREIGN PATENT DOCUMENTS

| | | |
|---|---|---|
| WO | 2020/049569 A2 | 3/2020 |

OTHER PUBLICATIONS

International Search Report for PCT International Application No. PCT/US2022/022741, dated Jun. 21, 2022.

*Primary Examiner* — Chu Chuan Liu
(74) *Attorney, Agent, or Firm* — RAPHAEL BELLUM PLLC

(57)          ABSTRACT

An oral fluid collection device includes a plunger and funnel to simultaneously collect and split a single specimen into metered doses for drug testing. The device may be used with collection tubes for collection of the metered doses and later testing. The device, when used, drives the metered dose into the collection tubes and removes bubbles in the specimen to provide improved accuracy in testing.

22 Claims, 15 Drawing Sheets

(58) Field of Classification Search
CPC ...... A61M 2005/3114; A61M 5/31511; A61M
1/67; A61M 5/204
See application file for complete search history.

(56) References Cited

U.S. PATENT DOCUMENTS

| | | |
|---|---|---|
| 9,199,043 B2 | 12/2015 | Chattaraj |
| 10,898,169 B1 | 1/2021 | Johnson |
| 2009/0004058 A1* | 1/2009 | Liang ................. A61B 10/0096 |
| | | 422/68.1 |
| 2014/0316302 A1 | 10/2014 | Nonnemacher |
| 2016/0123856 A1 | 5/2016 | Slowey |
| 2019/0381498 A1 | 12/2019 | Fruchter et al. |

* cited by examiner

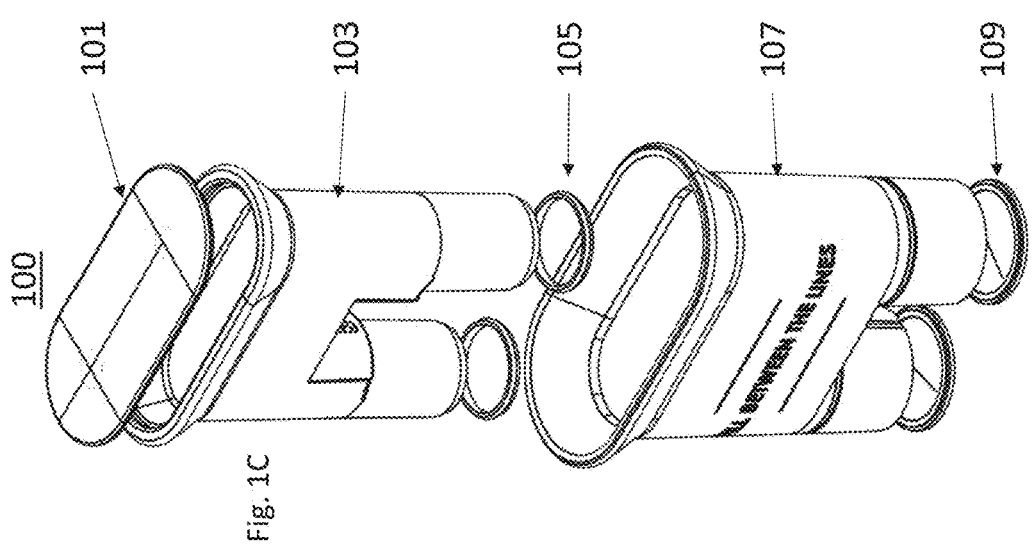
Fig. 1C
100
101
103
105
107
109
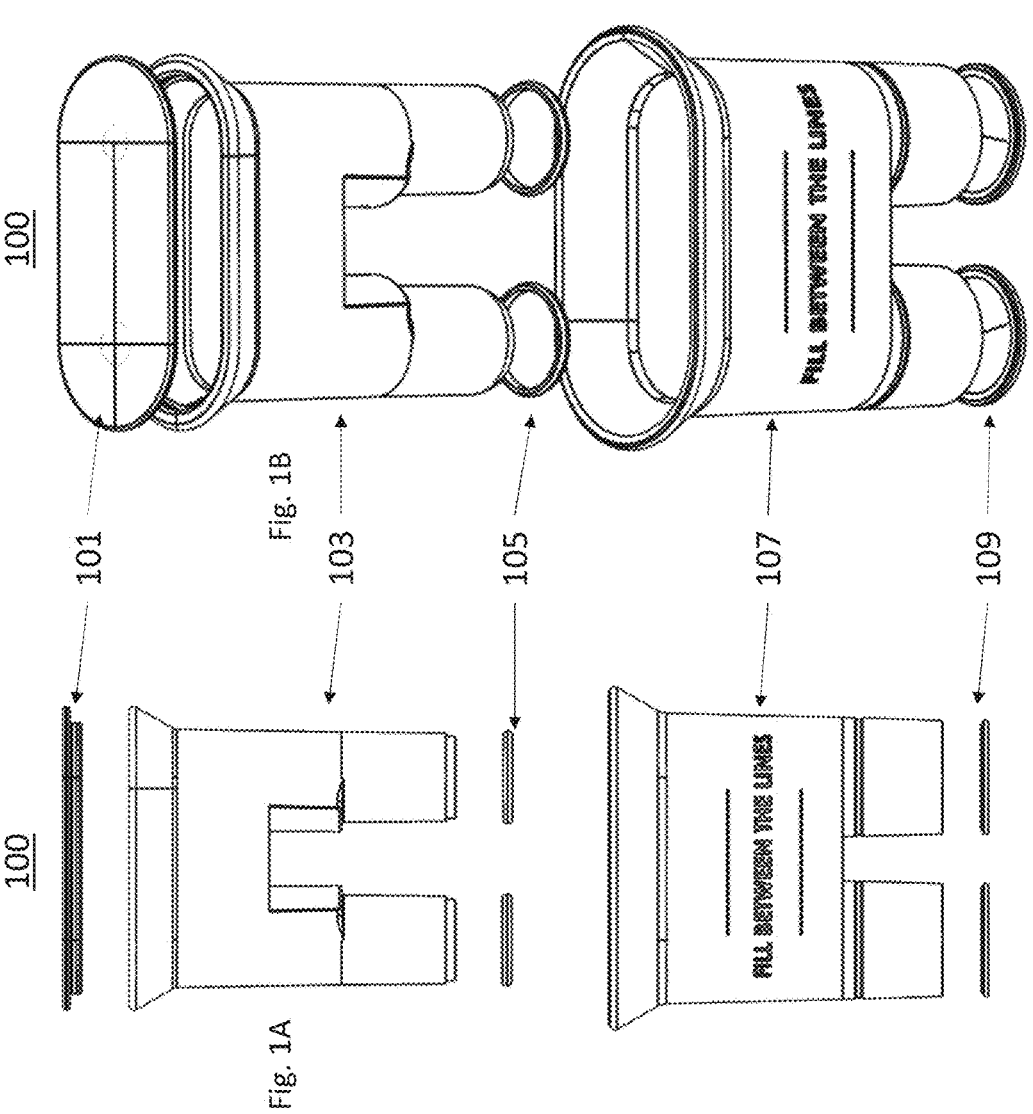
Fig. 1B
100
Fig. 1A
100
101
103
105
107
109
FILL BETWEEN THE LINES

103

103

105

107

103

100

107

200

100

107

200

100

107

300

301

ORAL FLUID COLLECTION DEVICE

CROSS-REFERENCE TO RELATED APPLICATION

This application claims benefit of priority from U.S. Provisional Application No. 63/179,780 filed on Apr. 26, 2021, the entire contents of which are incorporated by reference.

TECHNICAL FIELD

This invention relates to collection of fluids, and more particularly to devices and methods for the collection of oral fluid and methods for using a collection device for drug testing. In particular, the invention relates to a simultaneous split collection device that does not use a collection pad.

BACKGROUND

Drug testing has largely been relegated to blood and urine testing in the past due to consistency of results and detectability. In recent times, oral fluid testing has grown due to the benefits of being able to use a non-invasive testing method, advent of new technologies, ability to observe collection, testing at a point-of-care rather than in a laboratory, and shorter collection times that allow employees to return quickly to work. These benefits have started to outweigh a shorter window of detection. Sample collection methods may also influence the recovery of drugs in oral fluids.

At the moment, oral fluid specimens may be collected with various methods under guidelines from the United States Substance Abuse and Mental Health Services Administration (SAMHSA), the designated body responsible for regulating Federal drug testing in the United States. The key issues with specimen collection that are addressed by the guidelines relate to confirming specimen results with sampling from as near the same time as possible, to defined specimen volumes for collection, and to drug cut-off values and other requirements.

In particular, the SAMHSA guidelines point to oral fluid collection in: 1) two specimens collected simultaneously with two separate collection devices; 2) two specimens collected serially with two separate collection devices (requiring not more than two minutes between finishing the first specimen and beginning the second specimen); 3) two specimens collected simultaneously using a single collection device that directs the oral fluid into two separate collection tubes; and 4) a single specimen collected using a single collection device that is subsequently subdivided into two specimens. However, there are currently very few, if any, devices which do this for the third device where two specimens are collected simultaneously using a single collection device that directs the oral fluid into two separate collection tubes. Instead, conventional testing usually requires two collection devices which collect oral fluids serially, collect fluid simultaneously with multiple collection devices, or subdivide a single specimen. In the case of subdividing a single specimen, a collection pad that absorbs oral fluids is often used to collect and split a specimen. One issue with collection pads is the ability to recover 80% or more of drug and/or drug metabolite in the undiluted oral fluid. Every specimen collection must include at least 1 milliliter (mL) of oral fluid.

SUMMARY OF THE INVENTION

The systems and methods in accordance with the invention address a need to simultaneously collect a single specimen by directing it into two tubes. This minimizes the time of collection and simplifies the collection process by reducing the number of devices used to simultaneously collect a specimen in a single oral fluid collection device.

These systemic problems limit a user's ability to correctly use the sample collection devices and the ability to provide a collected sample that conforms to collection guidelines.

The invention provides an oral fluid collection device that meets SAMHSA guidelines for drug testing by providing a metered sample of collected oral fluids for testing using a single collection device and separate collection tubes. The oral fluid collection device increases efficiency in specimen collection by collecting multiple specimens simultaneously using a single collection device, and by not using collection pads before splitting a specimen. The oral fluid collection device volumetrically collects multiples specimens of equal volume.

BRIEF DESCRIPTION OF THE DRAWINGS

FIG. 1A is an exemplary exploded plan view of an oral fluid collection device in accordance with of the invention.

FIG. 1B is an exemplary exploded front perspective view of an oral fluid collection device in accordance with the invention.

FIG. 1C is an exemplary exploded front-side perspective view of an oral fluid collection device in accordance with the invention.

DETAILED DESCRIPTION OF THE INVENTION

Figures 2A, 2B:
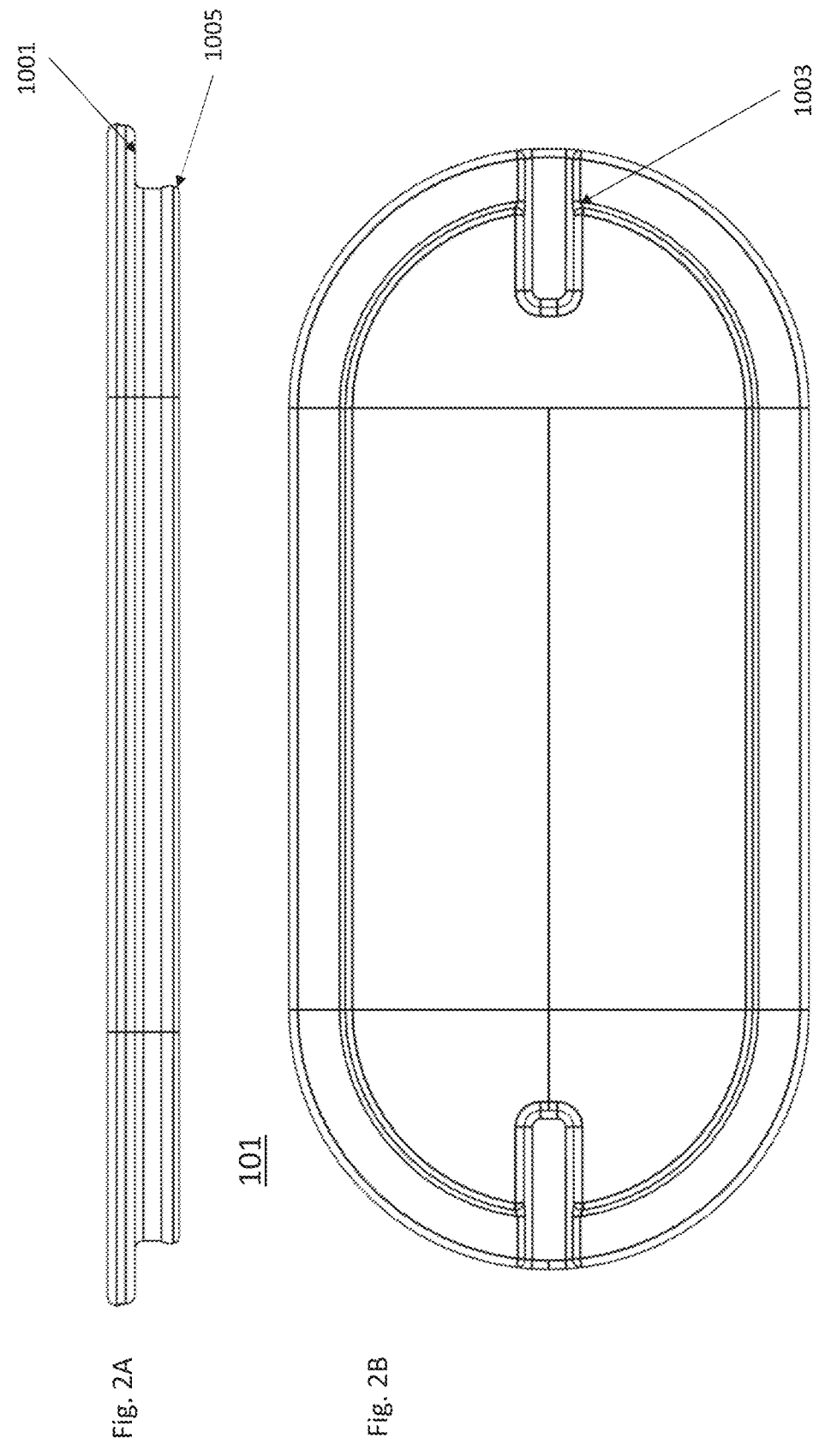
FIG. 2A is an exemplary front view of a cover for an oral fluid collection device in accordance with the invention.
FIG. 2B is an exemplary bottom view of a cover for an oral fluid collection device in accordance with the invention.
Figures 2C, 2D:
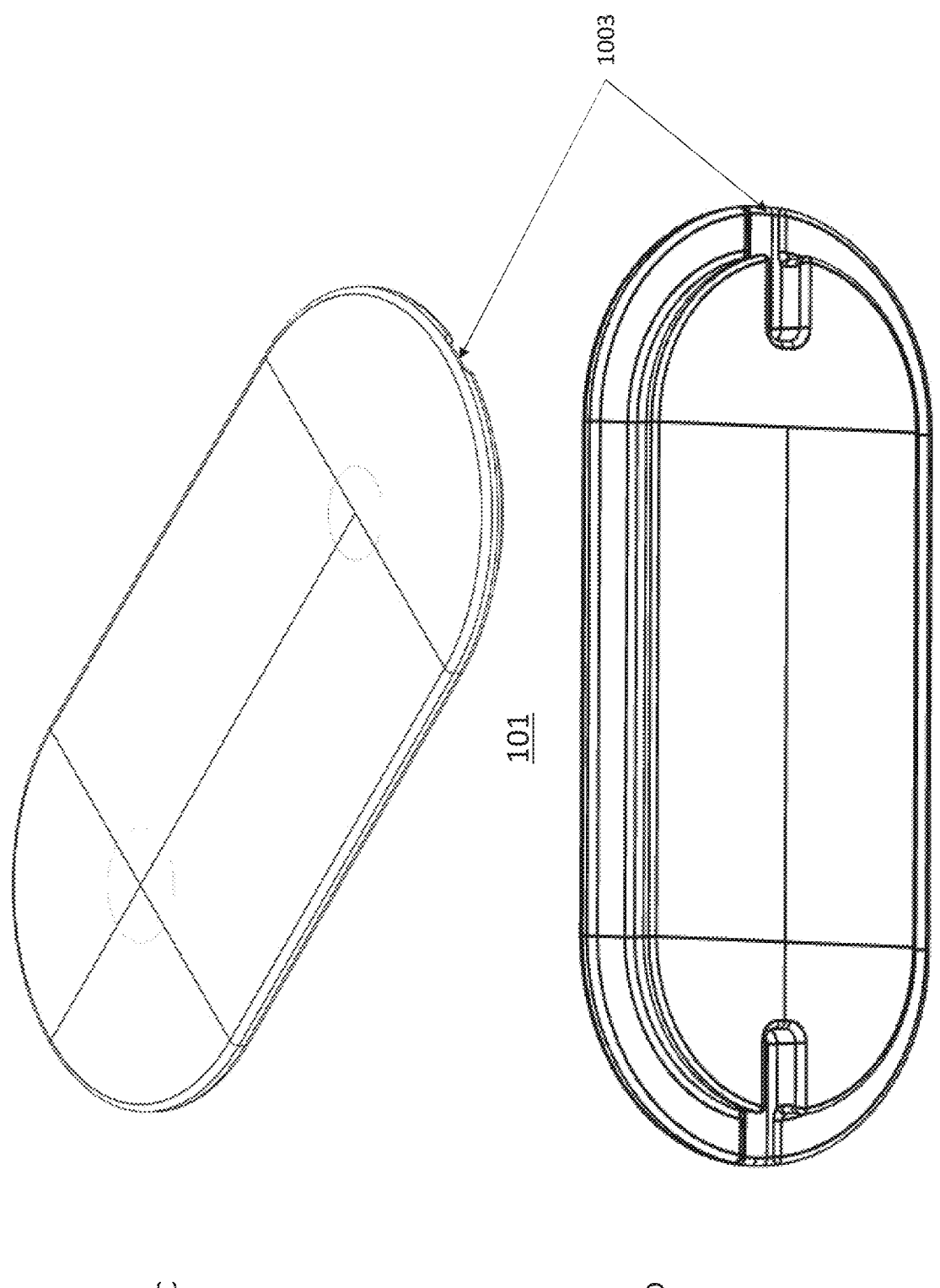
FIG. 2C is an exemplary perspective top view of a cover for an oral fluid collection device in accordance with the invention.
FIG. 2D is an exemplary perspective bottom-front view of a cover for an oral fluid collection device in accordance with the invention.

The invention provides an oral fluid collection device that collects at least two specimens without the use of multiple collection devices and/or collection pads.

FIGS. 1A-1C show exemplary exploded front plan view, exploded front perspective, and exploded front-side perspective views respectively of an oral fluid collection device in accordance with the invention. As shown, the oral fluid collection device 100 includes a cover 101, plunger 103, plunger seal 105, funnel 107, and valve 109. The cover 101 seals to the top of the plunger 103. The plunger seal 105 may be chemically (e.g., with adhesives) or physically (e.g., with a notched portion on the plunger) attached to the plunger 103. The plunger seal 105 seals the space between the outer wall at the bottom on the plunger 103 to the inner wall of the funnel 107. The valve 109 may also be chemically (e.g., with adhesives) or physically (e.g., with a notched portion on the funnel) attached to the funnel 107. Each part of the oral fluid collection device 100 is further described in detail below.

The oral fluid collection device 100 is made from one or more food and medical grade materials that cannot adulterate the specimen. The oral fluid collection device 100 is a dual funnel device that includes, as shown, two legs for substantially equal metering of a specimen into two tubes, vials or containers. In some embodiments, the funnel may include more than two legs, however, the plunger 103 and funnel 107 are designed to separate the specimen into substantially equal metered doses meeting the SAMHSA guidelines.

FIGS. 2A-2D show exemplary front view, bottom view, perspective top view, and perspective bottom views respectively of a cover for an oral fluid collection device. The cover 101 includes a capture edge 1001, edge cutouts 1003, and seal 1005. The cover 101 is shaped to match the top of the plunger 103 and seals to the top of the plunger 103 to provide a way to block overflow collected specimens from escaping the plunger. The capture edge 1001 provides an edge for the cover 101 to sit when placed on top of the plunger 103. The edge cutouts 1003, which are on opposite sides of the cover 101, provide air vents to allow air to escape from the plunger 103 when plunging a specimen out of the funnel 105 and into tubes 200. In some embodiments, there may be one or more edge cutouts 1003, however, the edge cutouts 1003 are generally evenly spaced along the edge of the cover 101. The seal 1005, as shown in FIG. 2A, includes a ridge along the edge of the cover 101 that may correspond and rest in a depression along the cover opening 2001 of the plunger 103. The seal 1005 may provide a tactile or audible feedback when set in the plunger 103 and prevents specimen overflow from escaping the plunger. In some embodiments, (not shown separately) the cover 101 may cap the plunger 103 with a ridged interior (i.e., hollowed center) that corresponds instead to a depression along the outer edge of the cover opening 2001 of the plunger 103, as long as the cover 101 prevents escape of specimen overflow. In some embodiments, the cover 101 is integrated into the plunger 103 as a single piece.

FIGS. 3A-3G show exemplary front, side, front-side perspective, front-bottom perspective, front-top perspective, top, and bottom views, respectively, of a plunger for an oral fluid collection device in accordance with the invention. The plunger 103 includes cover opening 2001, hard stop 2003, overflow channels 2005, seal adapter 2007, hollow body 2009, and legs 2011. The cover opening 2001 provides a resting edge for sealing the cover 101 to the plunger 103. The cover opening 2001 widens from the main body of the plunger 103 to correspond with the top the funnel 107 (i.e., funnel edge 3001 shown in FIG. 5A). Placing the plunger 103 in the funnel 107, such as in packaging for transport, the entire body of the oral fluid collection device 100 nests together so that only the funnel 107 is viewable from a front view when nested (see, e.g., FIG. 7D). In particular, as shown, the plunger 103 has a reciprocal or matching shape to the funnel 107. In some embodiments, only the portion of the plunger 103 that drives the specimen into the tubes, including the hard stop 2003, legs 2011, and seal 105 (i.e., the legs 2011, seal adapter 2007, and seal 105) nest with the funnel 107.

Figures 3A, 3B:
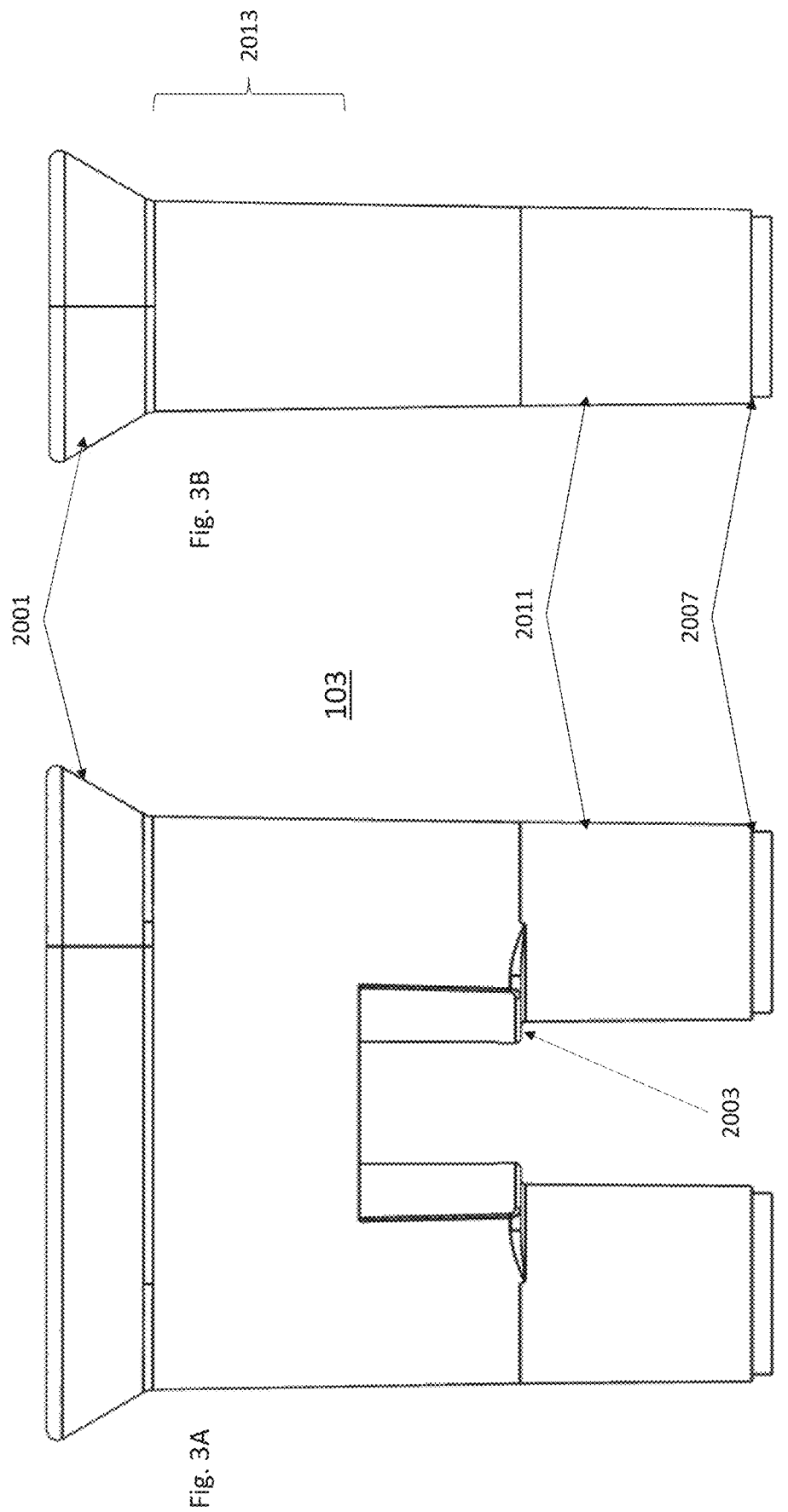
FIG. 3A is an exemplary front view of a plunger for an oral fluid collection device in accordance with the invention.
FIG. 3B is an exemplary side view of a plunger for an oral fluid collection device in accordance with the invention.
Figure 3C:
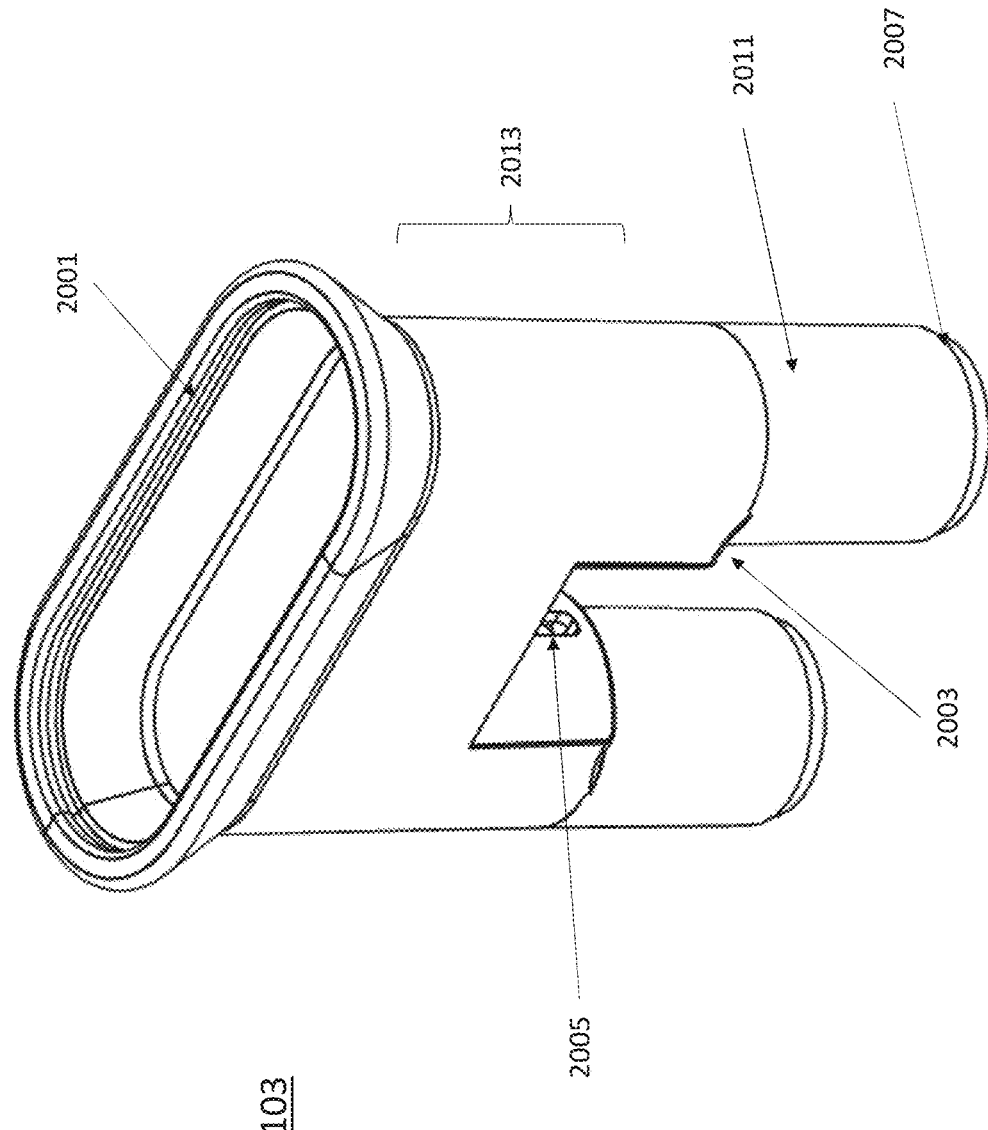
FIG. 3C is an exemplary front-side perspective view of a plunger for an oral fluid collection device in accordance with the invention.

Hard stop 2003 (see FIG. 3) limits the movement of the plunger 103 when pushed into funnel 107. The hard stop 2003 is a planar expansion on the legs of the plunger 103 that prevents the plunger 103 from pushing deeper than the hard stop edge 3007 of the funnel 107 (see FIG. 5A). This prevents the legs 2011 of the plunger 103 from extending past the valve 109 of the funnel 107. In some embodiments the hard stop 2003 may be on one leg and/or the other. As seen in FIG. 3A, the hard stop 2003 is between the bottom of the main body 2013 of the plunger 103 and the bottom of the legs 2011. Because the legs 2011 of the plunger 103 are longer than the legs 3011 of the funnel 107, when the plunger 103 is driven into the funnel 107, any excess specimen collected in the funnel 107 will remain in between the cavity created between the bottom of the main body 3013 of the funnel 107 and the bottom of the main body 2013 of the plunger 103, and between the legs 2011 of the plunger 103.

Figure 3D:
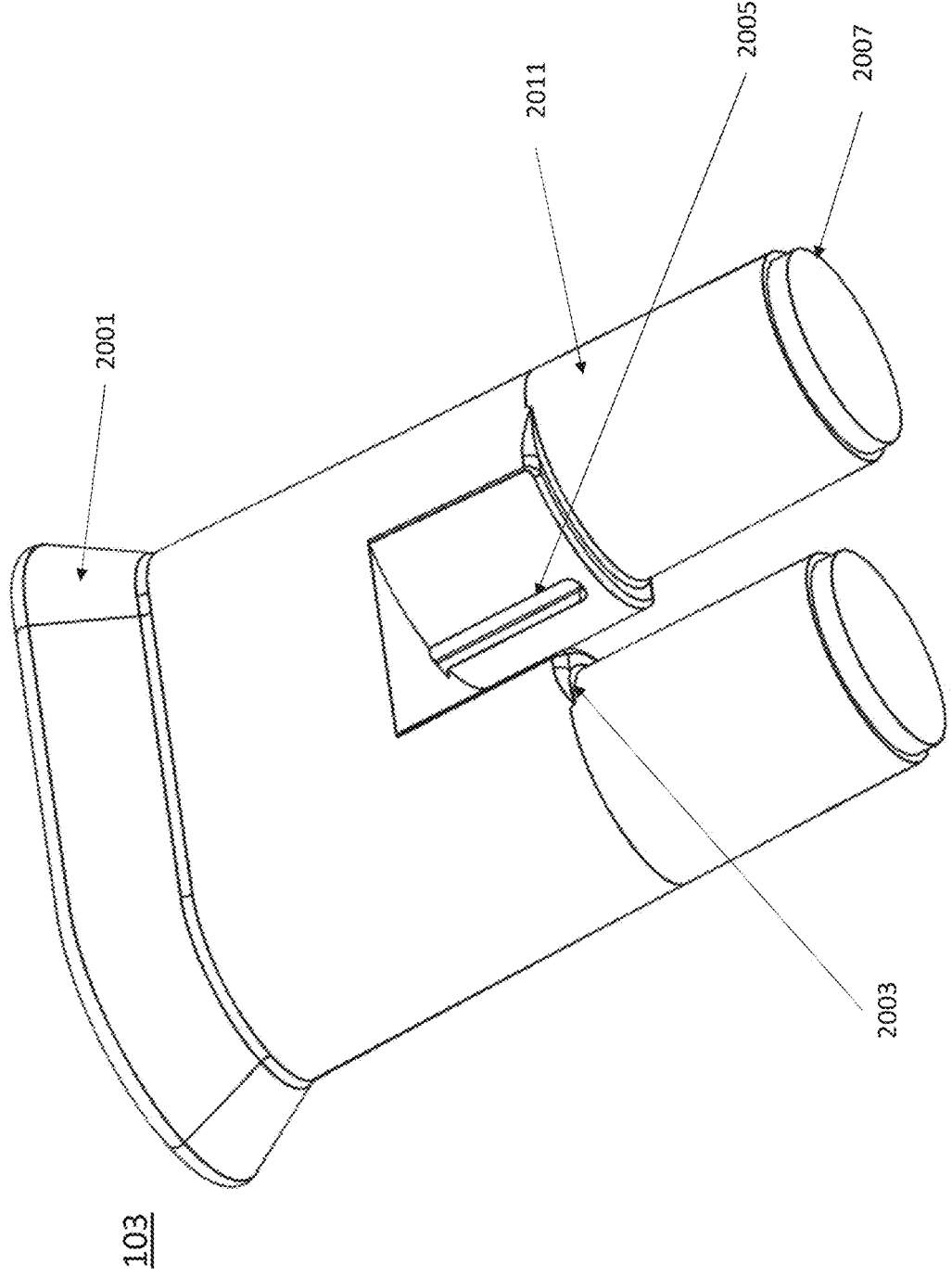
FIG. 3D is an exemplary front-bottom perspective view of a plunger for an oral fluid collection device in accordance with the invention.
Figure 3E:
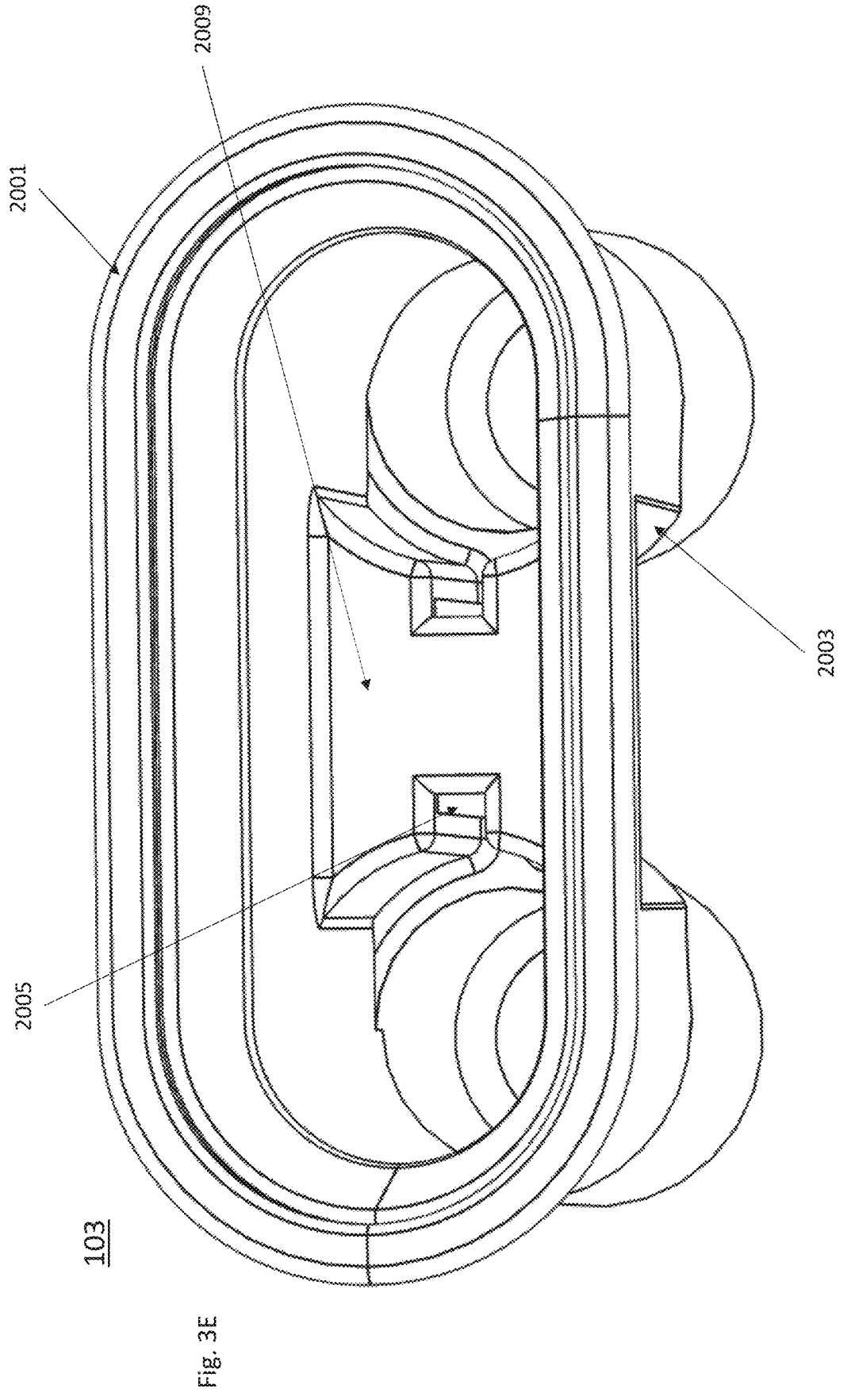
FIG. 3E is an exemplary front-top perspective view of a plunger for an oral fluid collection device in accordance with the invention.
Figures 3F, 3G:
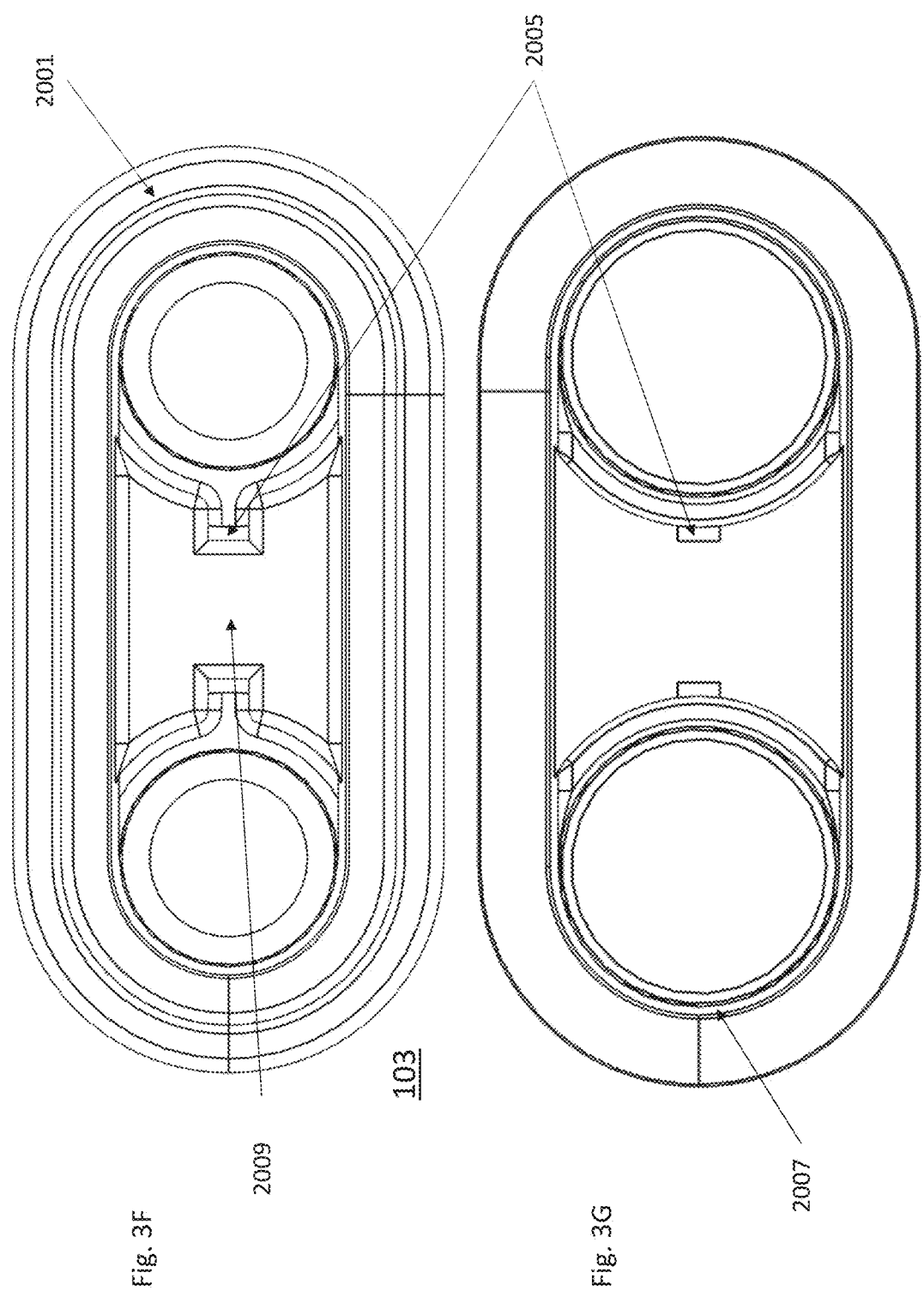
FIG. 3F is an exemplary top view of a plunger for an oral fluid collection device in accordance with the invention.
FIG. 3G is an exemplary bottom view of a plunger for an oral fluid collection device, of the invention.

The overflow channel 2005 is a narrow opening in the hollow body 2009 of the plunger 103. The overflow channel 2005 allows some specimen and air that may be contained in the main body 3013 of the funnel 107 (i.e., not within legs 3011 of the funnel 107) to be released into the plunger 103. This overflow specimen is a volume of specimen that exceeds the required 2 mL for testing (1 mL in each testing tube). The overflow specimen may also include a portion of the specimen that includes bubbling, which may affect volume measurements of the specimen. Additionally, overflow of the excess specimen will enter the plunger 103 in the hollow body 2009 through overflow channel 2005 to release air and displaced specimen and/or air as the plunger 103 is driven into the funnel 107. The overflow channel 2005, as shown in FIGS. 3D and 3E, runs along a section of legs 2011 and extends into a part of the hard stop 2003.

The seal adapter 2007 accepts plunger seal 105 onto the legs 2011 of the plunger 103. The seal adapter 2007 is shown to include a notch cut in from the rest of the leg 2011. See, for example, FIG. 3D. The notch cut provides a space for the plunger seal 105 to be seated and prevents accidental removal of the plunger seal 105 from the plunger 103. The plunger seal 105 may also be chemically attached to the plunger 103 by using adhesives to prevent the plunger seal 105 from moving when in use. The seal adapter 2007 provides a location along the outer wall of legs 2011 and near the closed end of the legs 2011 to seal the space between the funnel leg wall 3009 of the funnel 107 and outer wall of legs 2011 of the plunger 103 when driving the plunger 103 into the funnel 107.

Figure 4:
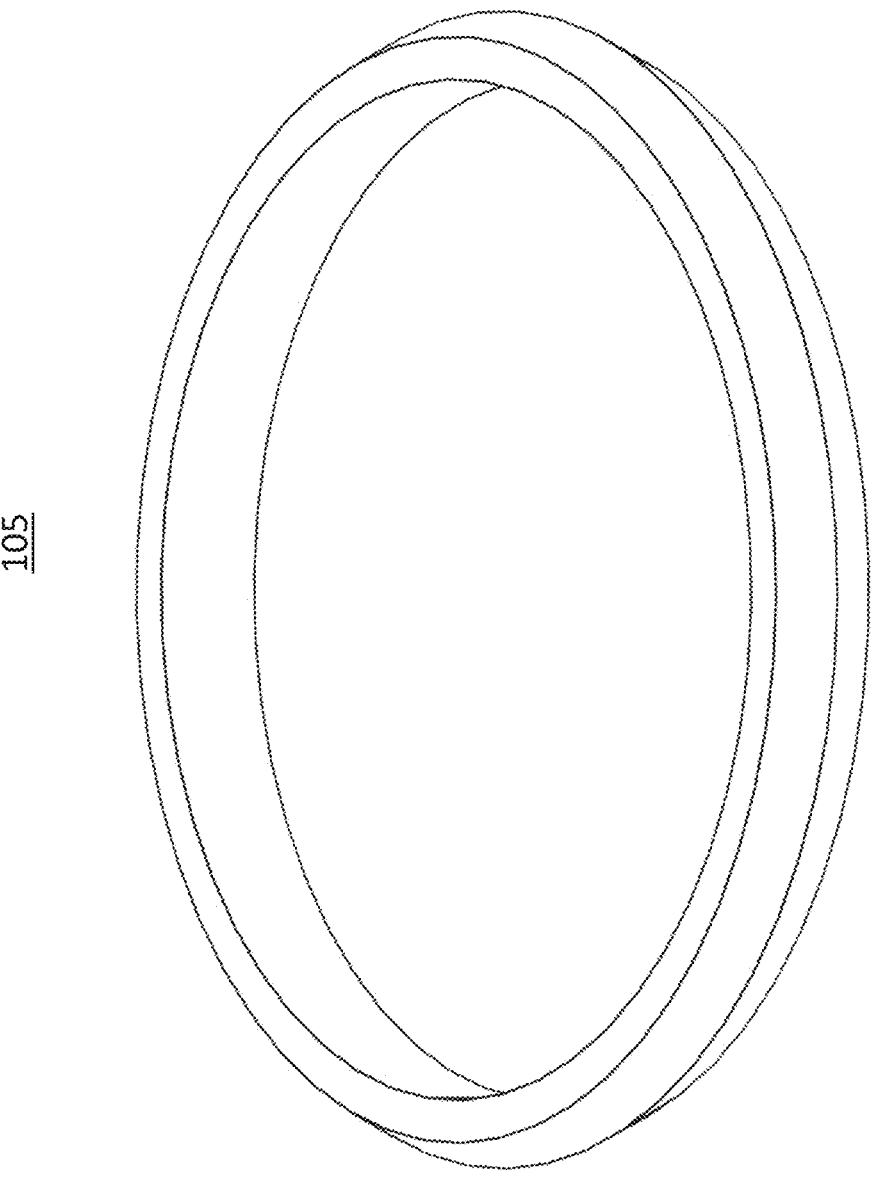
FIG. 4 is an exemplary top perspective view of a plunger seal for an oral fluid collection device in accordance with the invention.

FIG. 4 shows an exemplary top perspective view of a plunger seal 105 for an oral fluid collection device 100. The plunger seal 105 is a looped gasket similar to an O-ring creating a seal between the plunger 103 and funnel 107. The plunger seal 105 may be made of an elastomer, including thermoplastic elastomers, silicone, and rubber materials, which may seal the space between the leg 2011 of the plunger 103 and leg 3011 of the funnel 107.

FIGS. 5A-5F show exemplary front, side, front-side perspective, front-top perspective, top, and bottom views, respectively, of a funnel for an oral fluid collection device 100. The funnel 107 includes a funnel edge 3001, fill indicator 3003, tube adapter 3005, hard stop edge 3007, funnel leg wall 3009, legs 3011, main body 3013, and leg opening 3015. The funnel 107 is made of a translucent or transparent material that can show the amount of specimen (e.g. saliva) inside the funnel 107. The funnel edge 3001 provides an opening to allow a user to easily spit into the funnel 107. The funnel edge 3001 conforms to the shape of a human mouth and has an opening that expands from the main body 3013 of the funnel 107.

The fill indicator 3003 includes two fill lines and simple and clear instructions to "fill between the lines" when using the oral fluid collection device 100. The fill lines take foaming in oral specimens into account and include a minimum and maximum fill line to collect a metered volume of specimen of 1 mL per tube. The maximum fill line prevents too much overflow specimen filling the hollow body 2009 of the plunger 103, and provides a measured ratio of specimen to buffer solution or preservative of near 1 to 2. The fill indicator 3003 may include instructions in any language and lines or other indicators, such as a dot that can be used to compare the volume of provided specimen when the funnel 107 is level to the ground. In some embodiments, the fill indicator 3003 may also be indicated on the inside of the funnel 107 or seen from the inside of the funnel 107 to provide a clear and simple way for a user to determine whether they have met the specimen volume requirements for testing. In other words, a user may be able to see the line while collecting oral fluids from their mouth. The tube adapter 3005 includes a groove or thread for attaching tubes to the funnel for collection. In some embodiments, the tube adapter 3005 groove may snap or fasten the edge of the tubes in place to capture the tubes until the specimen is split into each tube for subsequent testing.

Continuing with FIG. 5, the hard stop edge 3007 corresponds with the hard stop 2003 (shown in FIG. 3A) to prevent the plunger 103 from being driven further into the funnel 107. The length L1 of the hard stop edge 3007 from the bottom of legs 3011 is determined based on the volume of specimen that may be driven by plunger 103 and is metered to drive 1 mL of specimen into each tube of each leg 3011. The length L1 is determined by the distance from the hard stop edge 3007 to the valve 109. In other words, for embodiments where the valve 109 is integrated into the funnel leg wall 3009, the length L1 is not determined by the hard stop edge 3007 to the bottom of legs 3011, but is determined by the length between the hard stop edge 3007 and location of the valve 109 in legs 3011.

Figures 5A, 5B:
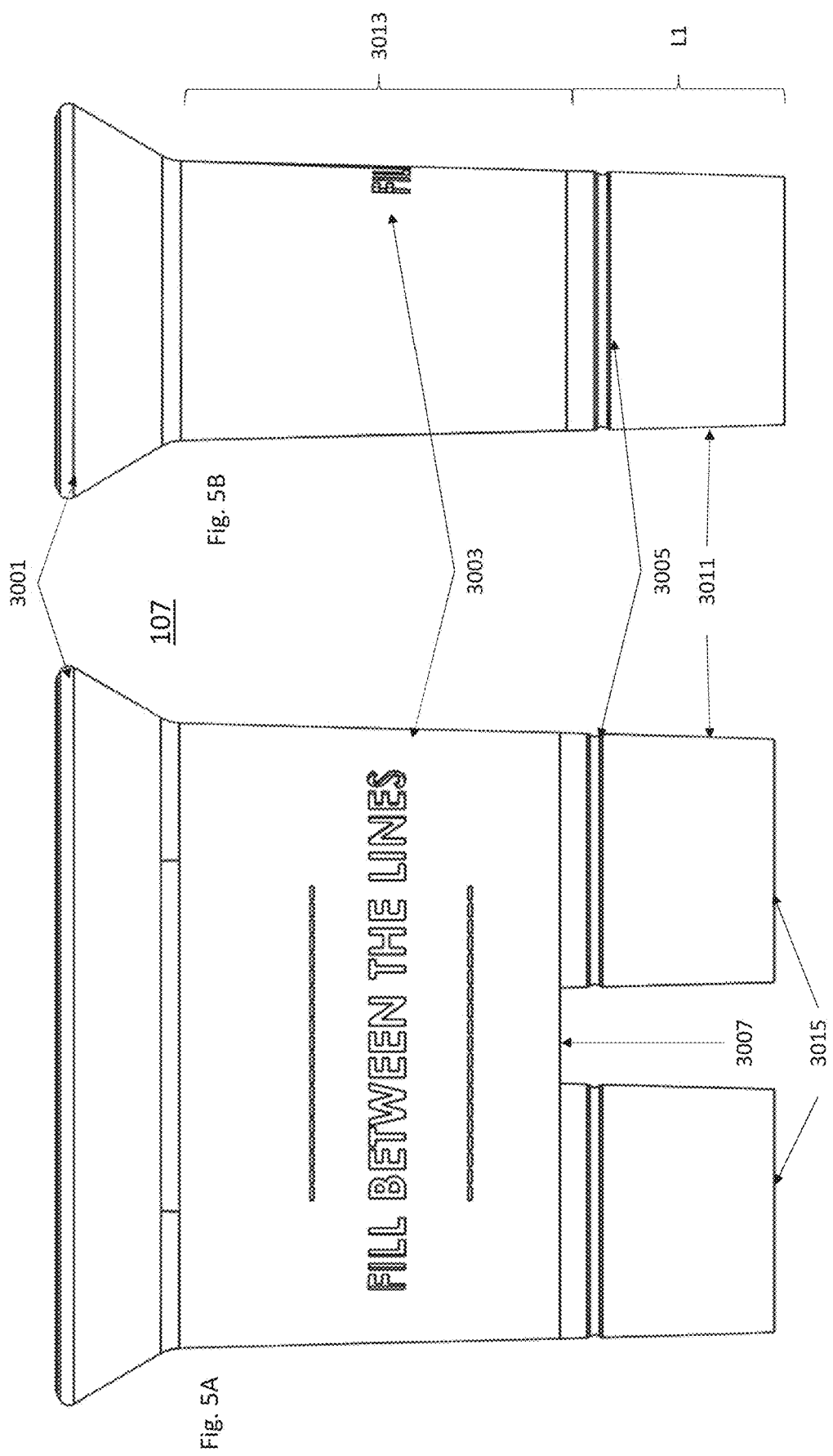
FIG. 5A is an exemplary front view of a funnel for an oral fluid collection device in accordance with the invention.
FIG. 5B is an exemplary side view of a funnel for an oral fluid collection device in accordance with the invention.
Figure 5C:
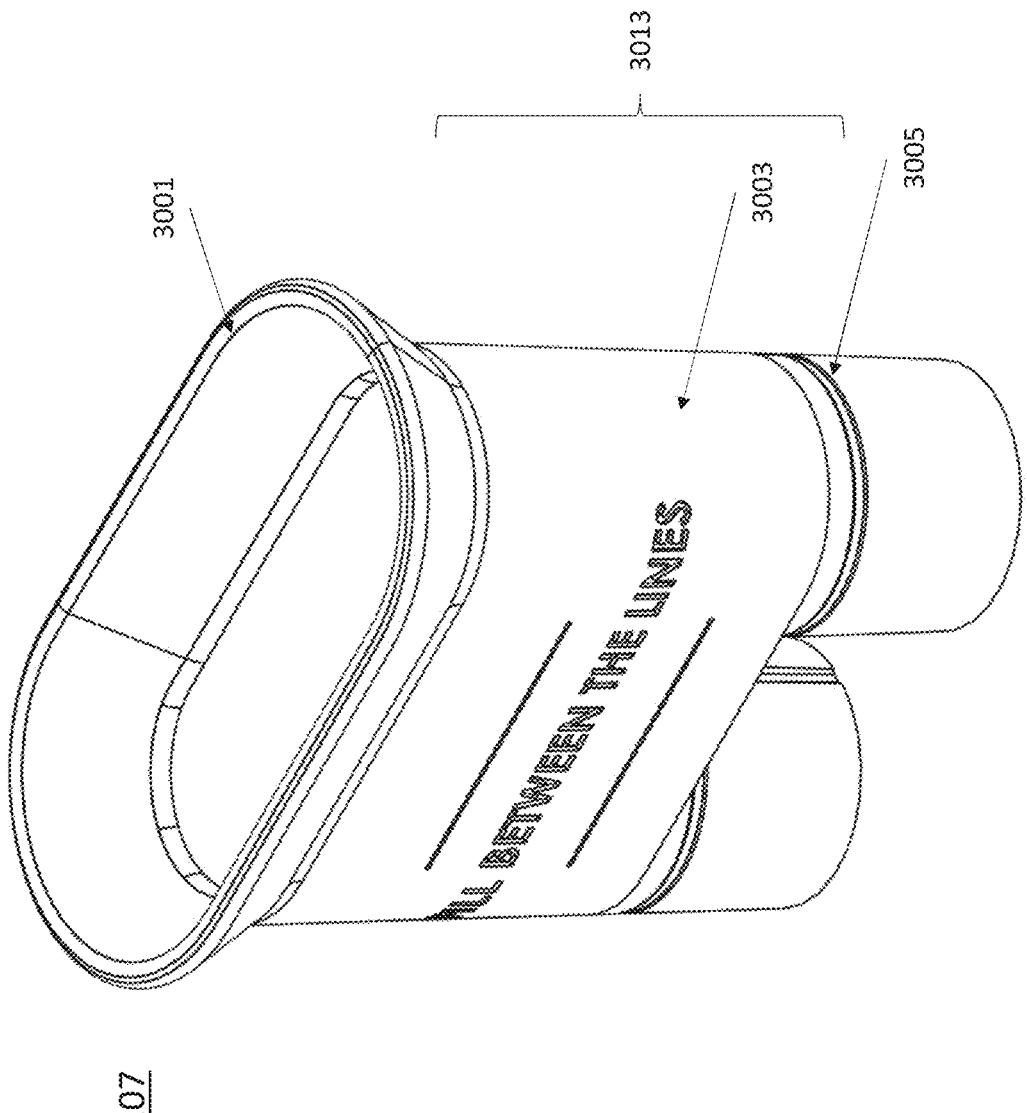
FIG. 5C is an exemplary front-side perspective view of a funnel for an oral fluid collection device, of the invention.
Figure 5D:
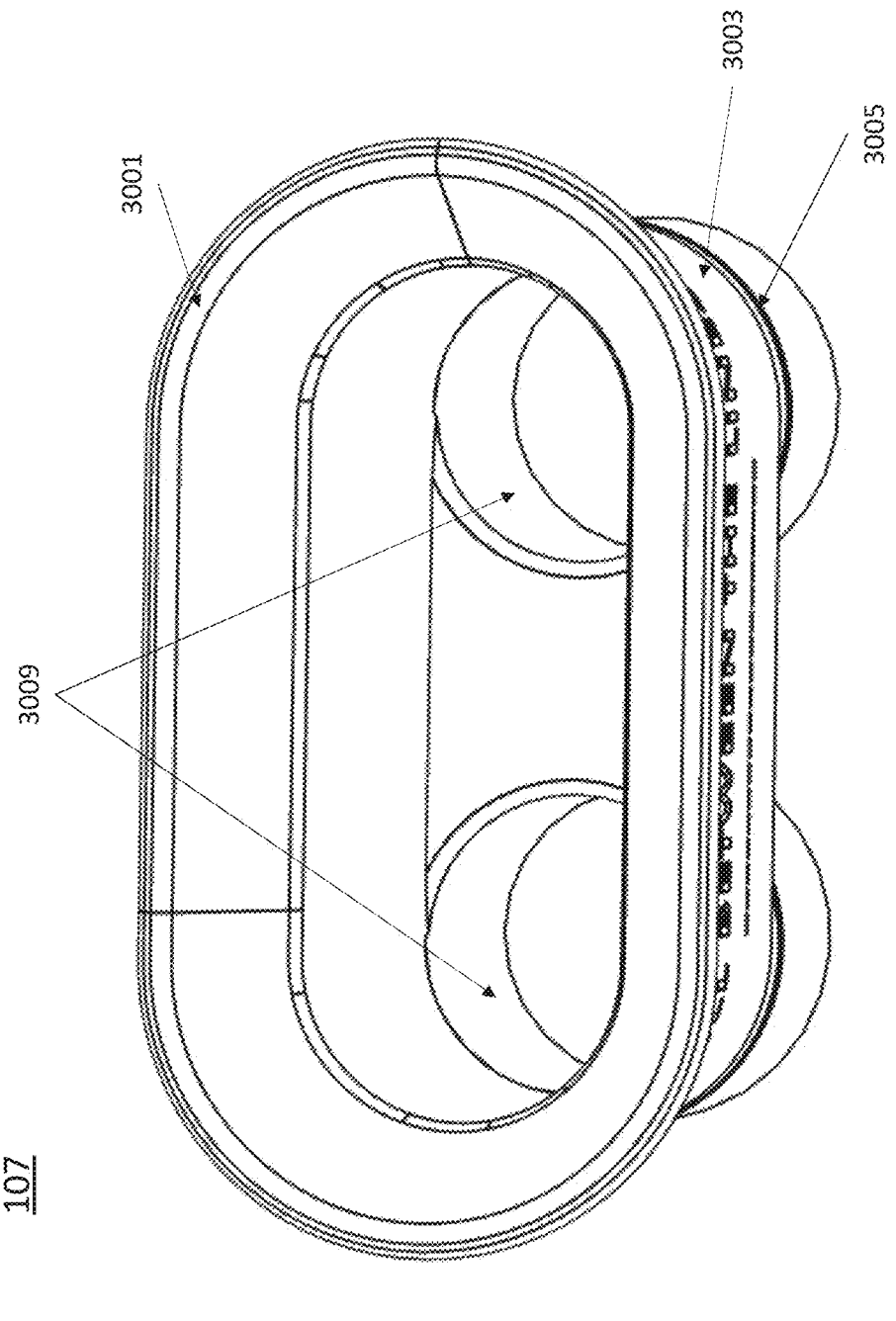
FIG. 5D is an exemplary front-top perspective view of a funnel for an oral fluid collection device in accordance with the invention.
Figures 5E, 5F:
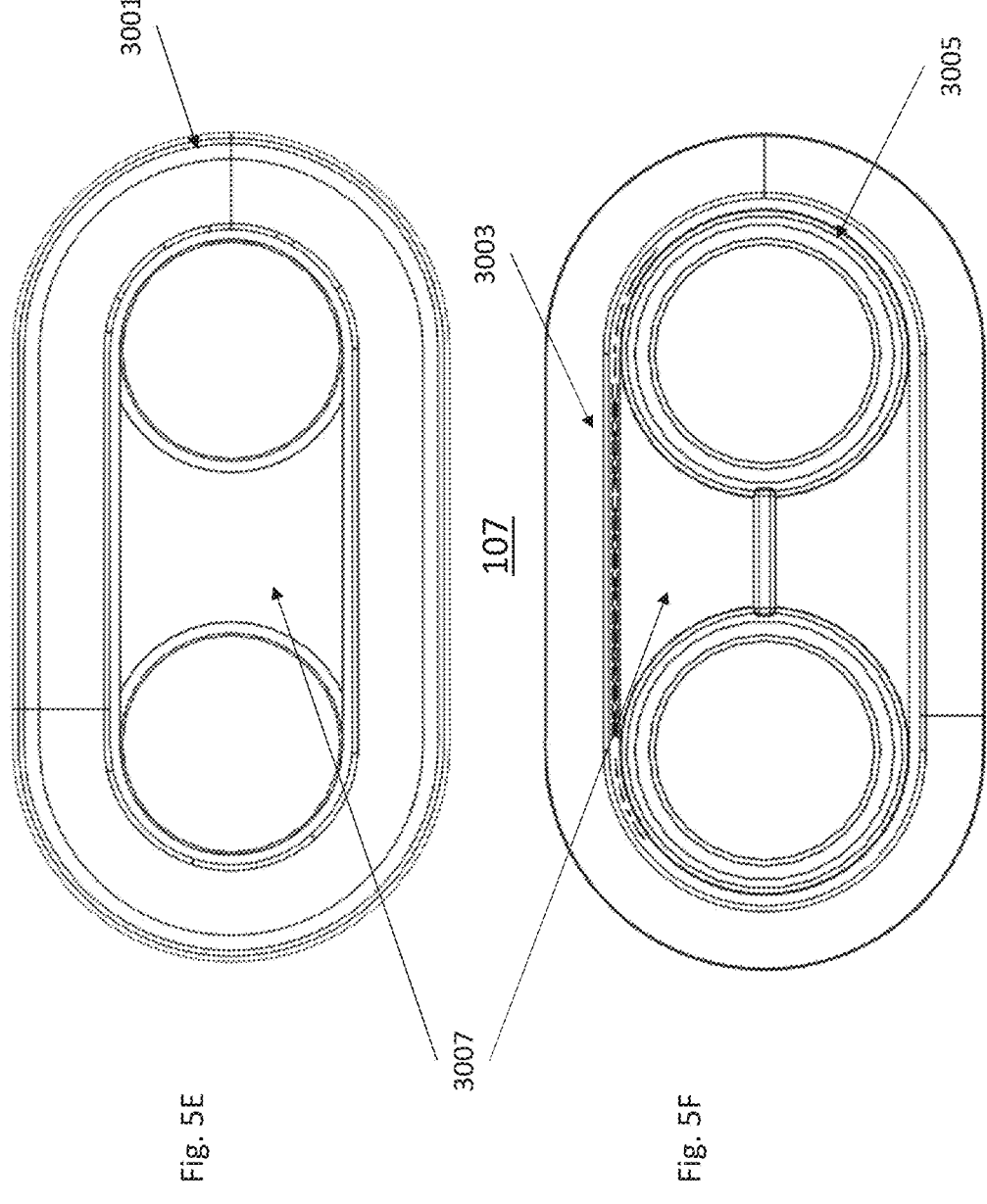
FIG. 5E is an exemplary top view of a funnel for an oral fluid collection device in accordance with the invention.
FIG. 5F is an exemplary bottom view of a funnel for an oral fluid collection device in accordance with the invention.

The legs 3011, as seen in FIG. 5A, have a slight tapering to easily allow a straight walled tube to be attached to the funnel 107. The funnel leg wall 3009, shown in FIG. 5D, is the interior wall of the funnel legs 3011. The funnel leg wall 3009 interfaces with the plunger seal 105 and is designed to seal against plunger legs 2011 to drive specimen in the funnel 107 into tubes for testing.

Figures 6A, 6B:
FIG. 6A is an exemplary front view of a valve for an oral fluid collection device in accordance with the invention.
FIG. 6B is an exemplary top perspective view of a valve for an oral fluid collection device in accordance with the invention.

The leg opening 3015 is an opening at the bottom of legs 3011 and is adapted to accept a valve 109 (see FIGS. 6A and 6B). In some embodiments, the leg opening 3015 may include an edge or other groove, threading, or ridge to retain the valve to the leg opening 3015 during use. The leg opening 3015 may also be prepped with an adhesive prior to placement of the valve 109 as an additional security measure to prevent removal of the valve 109 from the funnel 107.

FIGS. 6A and 6B show exemplary front and top perspective views illustrations respectively of a valve for an oral fluid collection device in accordance with the invention. The valve 109 includes a valve edge 4001 and valve opening 4003. In an exemplary embodiment, the valve 109 is overmolded to the leg opening 3015 of the funnel 107. In some embodiments, the valve 109 is attached to the leg opening 3015 with other chemical (e.g., with adhesives) or physical (e.g., with threading or notching) means. The valve 109 may, in some instances, be integrated into a leg 3011 (see FIG. 5A) of the funnel 107 and not at the bottom of the funnel 107. In those embodiments, the valve 109 is in a notch or groove in the funnel leg wall 3009.

As shown in FIGS. 6A and 6B, the valve 109 includes an edge 4001 to rest the valve within the leg opening 3015. The valve 109 is substantially planar to cover the cross-sectional area (opening) of the valve legs 3011. The valve opening 4003 is a re-sealing slit that opens from the pressure created by driving the plunger 105 into the funnel 107. The opening 4003 allows specimen collection without releasing collected specimen. However, when a force is applied to the valve 109 by driving the plunger 105 into the funnel 107, the valve opening 4003 opens enough to release specimen into tubes 200 that are attached to the funnel 107. Thus, the valve 109 includes a material, such as a food or medical grade elastomeric material, that can be overmolded, threaded, or inserted into the funnel legs 3011. Materials may include thermoplastic elastomers, rubber, and silicone materials. In some embodiments, the valve opening 4003 may prevent backflow and allow forward flow into the attached tubes.

In some embodiments, the valve 109 may have a non-planar shape such as a parabolically taper to a slit. In some embodiments, the valve 109 may include other opening types that seal when minimal force is applied to the valve 109 and allow forward flow when the plunger 103 is driven into the funnel 107. In some embodiments, the valves 109 include cross-slit valves, duck-bill valves, umbrella valves, dome valves, etc. that are closed or sealed until a force is applied to the valve 109, and re-sealed or closed once the force is removed. Once re-sealed, the oral fluid collection device 100 may safely be discarded. As the specimen is driven through the valve opening 4003, bubbles in the specimen are removed from the specimen collected in the tubes. Elimination of the bubbles increases the accuracy of the testing.

Figures 7A, 7B, 7C, 7D:
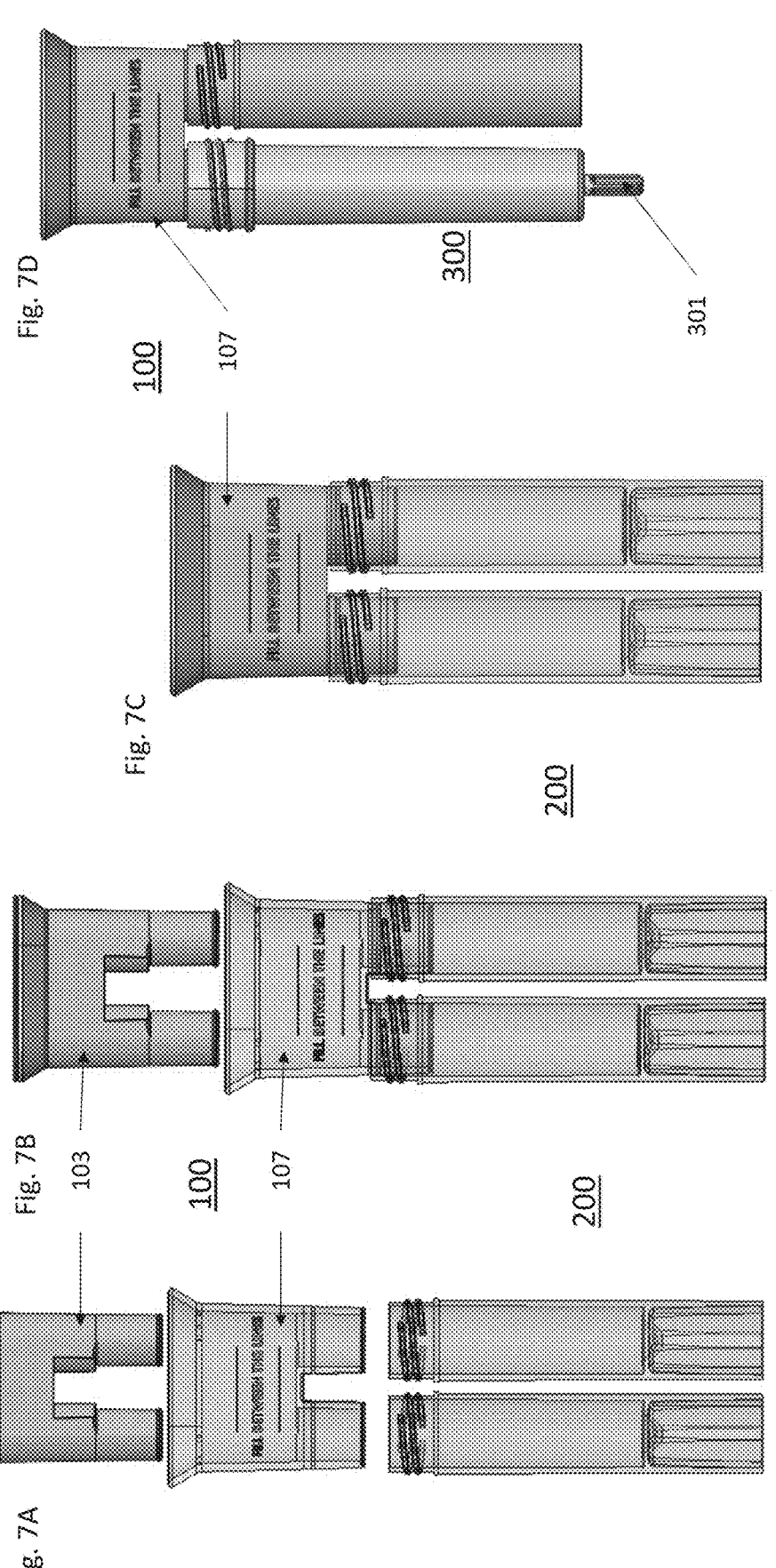
FIGS. 7A-C are exemplary front views of the oral fluid collection device of FIGS. 1A-6B in use with a specimen collection tube.
FIG. 7D is an exemplary front view of the oral fluid collection device of FIGS. 1A-6B in use with another specimen collection tube.

FIGS. 7A-C show exemplary front views of the oral fluid collection device of FIGS. 1A-6B in use with a specimen collection tube. FIG. 7A shows three major components (the plunger 103, the funnel 107, and the tubes 200) of the oral fluid collection device 100 prior to use. To make collection easier for the users, the specimen may be collected in the funnel 107 while the tubes 200 have not been attached. FIG. 7B shows the funnel 107 attached to tubes 200, but plunger 103 is not yet inserted into the funnel 107. At this stage, the specimen has been collected in funnel 107, but has not yet been driven into tubes 200. FIG. 7C shows the next stage where plunger 103 is driven into the funnel 107 while both the tubes 200 are attached. At this stage, 1 mL of the specimen has been driven into each of the tubes 200. The plunging and valves 109 remove the bubbles from the specimen.

FIG. 7D shows an exemplary front view of an oral fluid collection device of FIGS. 1A-6B in use with another specimen collection tube. Collection tube 300 includes an adapter 301 to seat the tube in a testing device or to allow a specimen to flow to a testing device.

The metered specimen may be mixed with around 2 mL of a buffer solution or preservative to obtain a 1:2 specimen to buffer ratio. The buffer solution may be added to the tubes 200 and 300 before the specimen is added from the funnel 107, or after the specimen has been added to the tubes 200 and 300 and the tubes 200, 300 are removed from the funnel 107.

In one exemplary embodiment, the oral fluid collection device is transported to a tester integrated together (i.e., the plunger in the funnel) or in separate pieces (e.g., funnel separate from the plunger) in one or more sterile pouches. The user may pull the collection device apart by pulling the cover off the plunger and then separating the plunger and funnel from one another. Once apart, the user may place a specimen into the funnel by spitting into the funnel. While spitting, the user may see the volume of specimen contained in the funnel due to transparency or translucency of the funnel. Based on the ability to see the volume and compare against the fill indicator on the outside or inside of the funnel, the user fills the funnel until the volume of specimen is between the fill lines. Once full, the user may hand the funnel to a test administrator. The test administrator or user, then splits the specimen into testing tubes by attaching or placing the funnel on top of two testing tubes. The administrator may then cover the plunger with the plunger cover, if uncovered, and then drive the plunger into the funnel on top of the testing tubes. As the plunger is driven into the funnel, the a metered volume of specimen in the funnel is driven through the funnel valves and into the testing tubes, meeting the requirement of 1 mL of specimen for each tube. Meanwhile, any overflow specimen is also released into the hollow body of the plunger through plunger overflow channels. Once the testing tubes are filled with specimen, a buffer or preservative may be mixed with the specimen at a 1:2 ratio. The buffer may have been provided with the tubes prior to split of the specimen into the tubes or may be added after the specimen has been split into the tubes. This then provides a prepped specimen for testing.

Although the invention has been described with reference to various exemplary embodiments, it is to be understood that these embodiments are merely illustrative of the principles and applications of the invention. Those having skill in the art would recognize that various modifications to the exemplary embodiments may be made without departing from the scope of the invention. Various features and/or characteristics of differing embodiments of the invention may be combined with one another. Any directional aspects of an oral fluid collection device of the invention as it is described, oriented, or appearing in the drawings are presented for convenience only; they are not intended to be limiting or to imply that the device has to be used or positioned in any particular orientation.

The claimed invention is:

1. An oral fluid collection device for drug testing, comprising:
   a funnel configured to collect a specimen of oral fluids, the funnel comprising one or more valves each switchable between an open state and a closed state; and
   a plunger configured to at least partially nest in and move relative to the funnel to split the specimen into two or more metered doses and cause the one or more valves to switch from the closed state to the open state and to drive the two or more metered doses of the specimen out of the funnel through the one or more valves in the open state.

2. The device of claim 1, wherein the funnel comprises two or more legs configured to collect the two or more metered doses, respectively.

3. The device of claim 1, wherein the funnel includes a translucent or transparent material.

4. The device of claim 3, wherein the funnel includes a fill indicator to verify a volume of the specimen has met a minimum and/or maximum volume.

5. The device of claim 4, wherein the fill indicator accounts for foaming of the specimen when collected.

6. The device of claim 1, wherein the plunger further comprises an overflow channel configured to direct overflow of the specimen and air to escape from an interior of the funnel into the plunger when the plunger is moved relative to the funnel.

7. The device of claim 6, wherein the plunger further comprises a cover to prevent the overflow of the specimen from escaping the plunger and an edge cutout in the cover for air to escape the plunger.

8. The device of claim 1, wherein the one or more valves are overmolded to the funnel.

9. The device of claim 1, wherein the plunger further comprises a hard stop for metering the two or more doses.

10. An oral fluid collection assembly for drug testing, comprising:
    a funnel configured to collect a specimen of oral fluids, the funnel comprising one or more valves each switchable between an open state and a closed state;
    a plunger configured to at least partially nest in and move relative to the funnel to split the specimen into two or more metered doses and cause the one or more valves to switch from the closed state to the open state and to drive the two or more metered doses of the specimen out of the funnel through the one or more valves in the open state; and
    two or more tubes to collect the two or more metered doses driven out of the funnel.

11. The device of claim 10, wherein the funnel comprises two or more legs configured to collect the two or more metered doses, respectively.

12. The device of claim 10, wherein the funnel includes a translucent or transparent material.

13. The device of claim 12, wherein the funnel includes a fill indicator to verify a volume of the specimen has met a minimum and/or maximum volume.

14. The device of claim 13, wherein the fill indicator accounts for foaming of the specimen when collected.

15. The device of claim 10, wherein the plunger further comprises an overflow channel configured to direct overflow of the specimen and air to escape from an interior of the funnel into the plunger when the plunger is moved relative to the funnel.

16. The device of claim 15, wherein the plunger further comprises a cover to prevent the overflow of the specimen from escaping the plunger and an edge cutout in the cover for air to escape the plunger.

17. The device of claim 10, wherein the one or more valves are overmolded to the funnel.

18. The device of claim 10, wherein the plunger further comprises a hard stop for contributing to metering the two or more metered doses.

19. A method of collecting a specimen of an oral fluid for drug testing, the method comprising:

providing the oral fluid collection assembly of claim 10;

collecting the specimen in the funnel of the oral fluid collection assembly;

driving the specimen from the funnel with the plunger of the oral fluid collection assembly to split the specimen into two or more metered doses; and collecting, via the one or more valves of the funnel, the two or more doses in the two or more tubes of the oral fluid collection assembly.

20. The method of claim 19, further comprising:

adding a buffer solution or preservative to the two or more tubes; and mixing the buffer solution or preservative and the two or more doses in the two or more tubes.

21. The method of claim 19, wherein each of the two or more metered doses is at least one milliliter (mL).

22. The method of claim 20, wherein a volume of the mixed buffer solution or preservative is about two milliliters (mL).

* * * * *